United States Patent
Yadav

[19]

[11] Patent Number: 6,083,258
[45] Date of Patent: Jul. 4, 2000

[54] LOCKING STENT

[76] Inventor: Jay S. Yadav, 735 Aran Dr., Roswell, Ga. 30076

[21] Appl. No.: 09/087,142

[22] Filed: May 28, 1998

Related U.S. Application Data

[60] Provisional application No. 60/047,995, May 28, 1997.

[51] Int. Cl.[7] .................................................. A61F 2/06
[52] U.S. Cl. ...................... 623/1.15; 623/1.16; 623/1.32
[58] Field of Search ............................................ 623/1, 12

[56] References Cited

U.S. PATENT DOCUMENTS

| | | | |
|---|---|---|---|
| 5,618,299 | 4/1997 | Khosravi et al. | 623/1 |
| 5,670,161 | 9/1997 | Healy et al. | 424/426 |
| 5,725,549 | 3/1998 | Lam | 623/1 |
| 5,735,872 | 4/1998 | Carpenter et al. | 623/1 |
| 5,876,419 | 3/1999 | Carpenter et al. | 623/1 |

*Primary Examiner*—David H. Willse
*Assistant Examiner*—Suzette J. Jackson
*Attorney, Agent, or Firm*—William H. Dippert; Cowan, Liebowitz & Latman, P.C.

[57] ABSTRACT

An expandable intraluminal stent able to resist axial compression, comprising a body portion having a generally cylindrical structure formed by a series of interconnected bars or struts, at least one of said struts being formed of two portions having overlapping free ends; and a plurality of teeth projecting on adjacent surfaces of said overlapping free ends; whereby said stent is expanded to allow said two portions of said at least one strut to overlap at said free ends, whereby said teeth on said adjacent surfaces of said overlapping free ends of said struts engage one another to retain said stent in its expanded shape.

4 Claims, 1 Drawing Sheet

LOCKING STENT

This application claims benefit of Provisional Application 60/047,995 filed May 28, 1997.

FIELD OF THE INVENTION

This invention relates to endoprosthesis devices, generally called stents, and, more particularly, to expandable stents that lock in place once installed within a corporeal lumen.

BACKGROUND OF THE INVENTION

Stents are generally tubular shaped devices that function to hold open a segment of a blood vessel or other anatomical lumen and are useful in the treatment of atherosclerotic stenoses in blood vessels. A wide variety of stents have been developed for treating diseases of the blood vessels and other tubular structures inside the body. Stents are particularly suitable for use in supporting and holding back a dissected arterial lining that can occlude the fluid passageway therethrough.

In order to accomplish precise placement of stents within a corporeal lumen and to ensure that a stent placed at a particular position within a body remains at that position, various means are employed. The currently available stents fall within two broad categories: balloon expandable and self-expanding.

A balloon expandable stent is attached onto the outside of an uninflated balloon, which is then introduced into the body vessel and expanded at the desired stent location, thereby also expanding the stent being carried by the balloon. The balloon is then deflated, leaving the expanded stent in place within the vessel. Balloon expandable stents have the advantage of being expandable to the exact diameter of the vessel into which they are being introduced, thus allowing for precise sizing. However, these stents are susceptible to external compression after implantation that can lead to loss of rigidity of the stent and perhaps even collapsing.

A self-expanding stent, which generally has an expanded stent position as its relaxed state, is introduced in a collapsed state into the body vessel and, upon triggering or release of a particular mechanism, is allowed to expand into its expanded, relaxed position. Self-expanding stents, on the other hand, are less susceptible to external compression but will expand only to a preset diameter. If the stent is undersized in comparison to the host vessel, the risk of stent migration within the vessel exists. Oversizing the stent relative to the host vessel, in order to ensure that the stent remains in place within the vessel, unfortunately increases the trauma to the vessel wall.

An ideal stent would have the precise sizing capabilities of the balloon-expandable stents and the compression resistance of the self-expanding stents.

U.S. Pat. No. 5,423,885 (Williams) shows an expandable, balloon intravascular stent that resists collapsing to a smaller diameter once it has been expanded to a larger diameter. However, the Williams stent is prevented from collapsing due to a plurality of protrusions on its outer surface that engage the walls of the artery or vessel into which it is disposed, thereby locking the stent in the larger diameter. This stent thus avoids radial collapse and axial displacement of the stent by use of protrusions that are anchored into the walls of the host vessel. This stent has the severe drawback of causing trauma and potential damage to the host vessel wall. It is desirable to provide a stent that will achieve these results without damaging the walls of the host vessel.

OBJECTS OF THE INVENTION

It is an object of this invention to provide an improved stent.

It is also an object of this invention to provide stents with precise sizing capabilities.

It is a further object of this invention to provide stents that are compression resistant.

It is another object of this invention to provide stents that lock in an expanded shape once expanded.

These and other objects of the invention will become more apparent in the discussion below.

SUMMARY OF THE INVENTION

The present invention is directed to providing a stent, adapted to be attached or implanted with a body vessel, that is designed to expand through use of a balloon catheter or some other means and to remain in the expanded state with an enlarged diameter by engaging of locking teeth on overlapping segments of longitudinally extending segments of the stent structure. The stent is formed by a truss structure, part of which has triangular segments with longitudinally-extending bases. The stent has a plurality of teeth or angled protrusions on the overlapping segments of the bases of the triangles that engage each other during expansion of the stent and prevent the stent from collapsing beyond the diameter already achieved.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which.

DETAILED DESCRIPTION OF THE INVENTION

Figure 1:
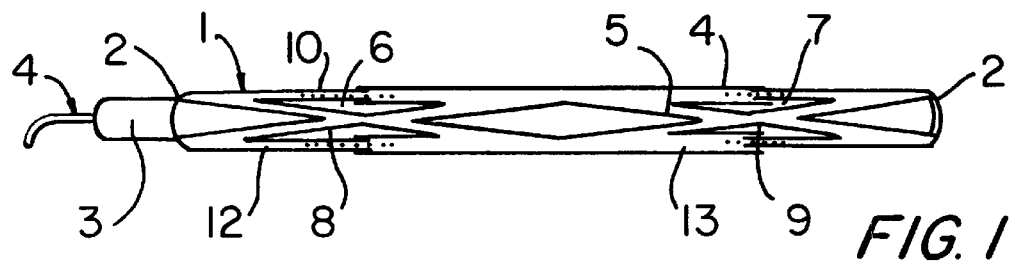
FIG. 1 shows a side elevational view of a balloon-expandable stent structure in accordance with an embodiment of this invention in an unexpanded position about an uninflated balloon.

This invention can perhaps be better appreciated by making reference to the drawings. In this invention, as illustrated in FIG. 1, a balloon-expandable stent structure 1 is formed in a generally tubular or cylindrical shape with an opening 2 at each stent end. In a preferred embodiment of the invention, stent 1 can be constructed of a variety of metallic or non-metallic alloys. The composition of the alloy of stent 1 is geared to provide strength and rigidity. Other compositions of stent 1 can be used without departing from the principles of this invention.

In the preferred embodiment of this invention, stent 1 is constructed of bars or struts 5 that intersect, interconnect and interlock in a truss structure format in order to provide rigidity during its expanded shape within the body vessel. One fundamental geometrical structural sub-unit of stent 1 is the triangle, since it is believed to be among the most rigid of the geometrical shapes. As shown in FIG. 1, stent 1 is formed with triangle substructures 6,7,8,9 as some of its rigid support units. As will be described herein, the bases 10,11,12,13 of triangle substructures 6–9 will lock relative to each other during expansion of stent 1 so that stent 1 is locked in its expanded shape.

As illustrated in FIG. 1, struts 5 of stent 1 are generally interconnected to form a truss-like structure for stent 1. FIG. 1 shows stent 1 in its collapsed state about the distal end of an uninflated balloon 3 of a balloon catheter 4. In its collapsed state, stent 1 has a relatively smaller diameter and a larger length that it does in its expanded state shown in FIG. 2. Bases 10–13 of triangle substructures 6–9, which lie in a longitudinal direction relative to stent 1, are formed by overlapping members 10'–13' and 10"–13". The ends of members 10'–13' and 10"–13" are separated during the collapsed state of stent 1 but, as will be discussed below, join with a slight overlap as bases 10–13 of triangles 6–9 shorten during stent expansion.

Figure 3:
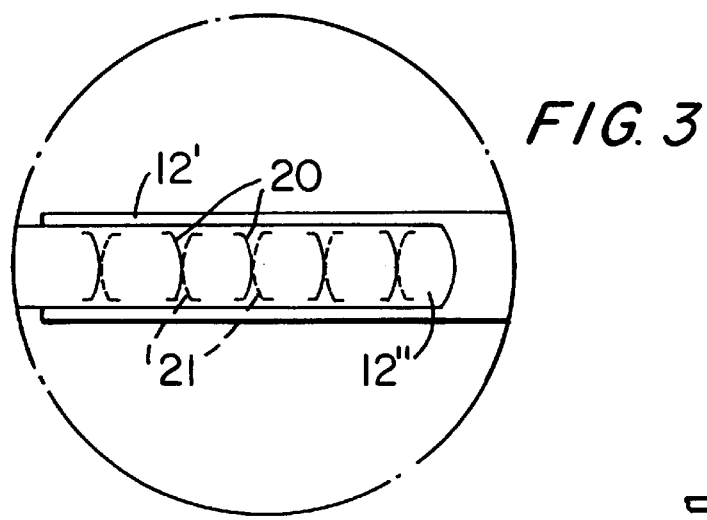
FIG. 3 shows a close-up side elevational view of the locking portion of the balloon-expandable stent structure of this invention.
Figure 4:
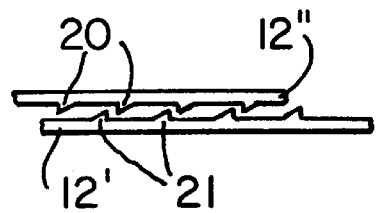
FIG. 4 shows a cross-sectional view of the locking portion of the balloon-expandable stent structure of this invention.

As illustrated in FIGS. 3 and 4, the terminal adjacent surfaces of longitudinally-extending, overlapping members 10'–13' and 10"–13" are provided with small ridges or angled teeth 20,21 that face in opposing directions so as to allow relatively easy passage of the ends relative to each other in one direction, i.e., to allow overlapping. However, these same teeth 20,21 prevent separation of the ends once overlapping has occurred.

Figure 2:
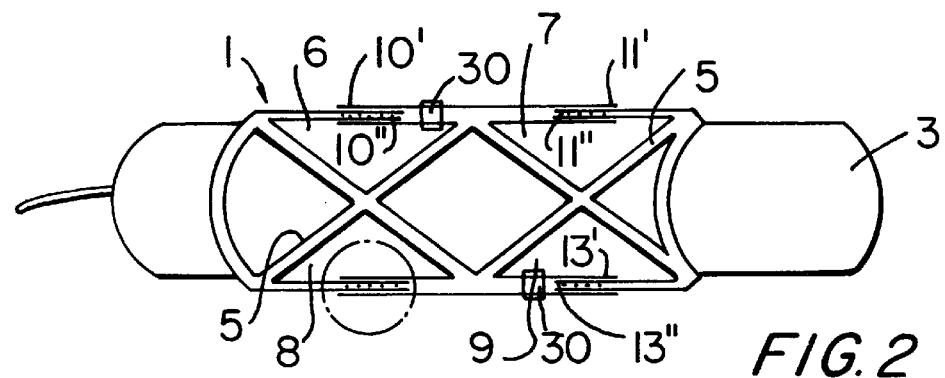
FIG. 2 shows a side elevational view of the balloon-expandable stent structure of this invention in an expanded position about an inflated balloon.

Typically, balloon 3, carrying stent 1, is then introduced into the body vessel at the distal end of balloon catheter 4 and is expanded at the desired stent location, thereby also expanding stent 1 which is carried by balloon 3, as shown in FIG. 2. Expansion of stent 1 causes bases 10–13 of triangle substructures 6–9 to shorten correspondingly, thereby causing the ends of members 10'–13' and 10"–13" to move towards each other in the direction of arrows A and B, respectively, into an overlapping relationship, as illustrated in FIG. 3. Movement of the ends of members 10'–13' and 10"–13" in the respective direction of arrows A and B is permitted due to the angles of teeth 20,21. Balloon 3 is then deflated, leaving stent 1 in its expanded state in place within the vessel.

Further expansion (increase in the radius of curvature) of stent 1 would be possible, as the ends of members 10'–13' and 10"–13" move further towards each other in the direction of arrows A and B, respectively, into a further overlapping relationship. However, collapse (decrease in the radius of curvature) of stent 1 would be prevented by the fact that teeth 20,21 engage with each other and do not permit movement of members 10'–13' and 10"–13" in the directions opposite to the directions of arrows A and B. In this way, expansion of stent 1 would be allowed, and stent 1 would be locked in its expanded state from collapsing.

Certain structural members may have slidably arranged, cooperating, short U-shaped segments 30 on the base segments. These segments 30 will undergo compensatory lengthening when the base segments shorten. This will minimize shortening of stent 1 and reserve the initial length of stent 1.

The use of a triangular cell structure of stent 1 with locking bases 10–13 of triangle substructures 6–9 leads to exceptional resistance of stent 1 to radial compression. The resulting radial strength of this stent 1 due to use of this geometry allows use of very narrow struts 5, which leads to a very low profile of the collapsed stent and increased longitudinal flexibility. Further increase in the longitudinal flexibility may be necessary for some applications and can be obtained by making cuts in some of the U-shaped connecting segments. This will further increase longitudinal flexibility of stent 1 without compromising its radial rigidity.

Stent 1 is particularly useful in applications where radial strength of stent 1 is critical, such as in treating aortic disease particularly for anchoring endovascular grafts for the treatment of abdominal aortic aneurysms.

It will be further apparent to one skilled in this art that the improvements provided for in the present invention, while described with relation to certain specific physical embodiments, also lend themselves to being applied in other physical arrangements not specifically provided for herein, which are nonetheless within the spirit and scope of the invention taught here.

I claim:

1. An expandable intraluminal stent able to resist axial compression, comprising:

a body portion having a generally cylindrical structure formed by a series of interconnected structural members, at least one of said structural members being formed of two portions having overlapping free ends; and a plurality of teeth projecting on adjacent surfaces of said overlapping free ends, wherein said stent is expanded to allow said two portions of said at least one structural member to overlap at said free ends, wherein said teeth on said adjacent surfaces of said overlapping free ends of said structural member engage one another to retain said stent in its expanded shape, and wherein at least some of said interconnecting structural members form a triangular substructure having a base structural member and two angled structural members wherein said base structural member of said triangular substructure is formed of two portions having overlapping free ends.

2. The expandable stent of claim 1 wherein said stent is capable of being carried into a vessel in a collapsed state on a balloon catheter and expanded thereby into an expanded state.

3. The expandable stent of claim 1 wherein at least some of said interconnecting structural members form a triangular substructure having a base structural member and two angled structural members, wherein said base structural member of said triangular sub-structure is formed of two portions having overlapping free ends.

4. The expandable stent of claim 3 wherein said base structural member extends longitudinally with respect to said cylindrical structure of said stent.

* * * * *